(12) United States Patent
Strang et al.

(10) Patent No.: US 10,821,282 B2
(45) Date of Patent: Nov. 3, 2020

(54) SHAPED MONOLITHIC CONTROLLED RELEASE DEVICE FOR IMPROVED DRUG RELEASE IN IMPLANTABLE MEDICAL LEADS AND LEADLESS PACEMAKERS

(71) Applicant: PACESETTER, INC., Sylmar, CA (US)

(72) Inventors: Tyler J. Strang, Valencia, CA (US); Benjamin F. James, IV, Valencia, CA (US); Matthew Malone, Burien, WA (US)

(73) Assignee: Pacesetter, Inc., Sylmar, CA (US)

( * ) Notice: Subject to any disclaimer, the term of this patent is extended or adjusted under 35 U.S.C. 154(b) by 247 days.

(21) Appl. No.: 15/984,697

(22) Filed: May 21, 2018

(65) Prior Publication Data

US 2019/0351222 A1 Nov. 21, 2019

(51) Int. Cl.
*A61N 1/05* (2006.01)
*A61N 1/375* (2006.01)
*A61M 5/172* (2006.01)
*A61N 1/365* (2006.01)
*A61N 1/372* (2006.01)

(52) U.S. Cl.
CPC ......... *A61N 1/0575* (2013.01); *A61N 1/3756* (2013.01); *A61M 5/1723* (2013.01); *A61N 1/365* (2013.01); *A61N 1/37252* (2013.01)

(58) Field of Classification Search
CPC ... A61N 1/0575; A61N 1/0568; A61N 1/3756
See application file for complete search history.

(56) References Cited

U.S. PATENT DOCUMENTS

| | | | | |
|---|---|---|---|---|
| 4,506,680 A | * | 3/1985 | Stokes | A61N 1/0568 424/424 |
| 4,844,099 A | * | 7/1989 | Skalsky | A61N 1/0565 607/120 |
| 6,052,625 A | * | 4/2000 | Marshall | A61N 1/056 607/122 |
| 2009/0024197 A1 | | 1/2009 | Jensen | |
| 2011/0125241 A1 | | 5/2011 | Cobian et al. | |

* cited by examiner

*Primary Examiner* — George R Evanisko
(74) *Attorney, Agent, or Firm* — Polsinelli PC (57) ABSTRACT

Disclosed herein is an implantable medical device for implantation against cardiac tissue in the administration of electrotherapy to the cardiac tissue. The device includes a distal end and a monolithic controlled release device. The distal end includes a housing structure and a cavity within the housing structure. The cavity opens exterior the implantable medical device via a distal opening. The monolithic controlled release device is within the cavity and proximal the distal opening. The monolithic controlled release device includes a distal face, a proximal face opposite the distal face, an outer circumferential surface extending between the distal face and the proximal face, and a spline-shaped inner lumen extending between the distal face and the proximal face and radially inward from the outer circumferential surface. The monolithic controlled release device further includes an active pharmaceutical ingredient.

20 Claims, 8 Drawing Sheets

SHAPED MONOLITHIC CONTROLLED RELEASE DEVICE FOR IMPROVED DRUG RELEASE IN IMPLANTABLE MEDICAL LEADS AND LEADLESS PACEMAKERS

FIELD OF THE INVENTION

The present disclosure is directed to implantable medical devices such as, for example, cardiac rhythm management pacing and defibrillation leads and leadless pacemakers. More specifically, the present disclosure is directed to monolithic controlled release devices that are part of an implantable medical device and release an active pharmaceutical ingredient at the implant site.

BACKGROUND OF THE INVENTION

Implantable cardiac rhythm management devices (ICRMD) such as implantable cardiac leads, which are used for pacing and/or defibrillation, and leadless pacemakers employ monolithic controlled release devices (MCRD) near the distal tip of such ICRMD. The MCRD carries an active pharmaceutical ingredient (API) and is located at the distal tip so the MCRD is in close proximity to, if not in actual physical contact with, the cardiac tissue at the implantation site. The close proximity of the MCRD to the cardiac tissue facilitates the API contacting the cardiac tissue, the API including an anti-inflammatory and/or other medicament(s) beneficial to the interaction of the cardiac tissue with the implanted aspects of the ICRMD.

ICRMD employing MCRD require analytical testing prior to release as a product. Analytical tests typically include chemical identification, assay, content uniformity, impurities and degradants, drug release (dissolution), particulate matter, bacterial endotoxin, and sterility. Drug release testing is particularly challenging since it can be affected by MCRD placement within the ICRMD. MCRD manufacturing, excipient chemistry, API chemistry, drug release test method, and ICRMD design.

Drug release testing with the MCRD may occur as an unattached MCRD, a distal subassembly of an ICRMD and/or a finished ICRMD for lot release testing as well as for annual stability testing. Elution testing follows USP <711> and/or USP <724> methods and acceptance criteria.

In the context of MCRD equipped ICRMD, there is a need in the art for improved drug release consistency and greater ease of release of the overall percentage of API. Improved consistency and greater drug release will improve MCRD yield, reduce product scrap, and provide more consistent anti-inflammatory treatment by the API at the implant site.

SUMMARY

Disclosed herein is an implantable medical device for implantation against cardiac tissue in the administration of electrotherapy to the cardiac tissue. In one embodiment, the device includes a distal end and a monolithic controlled release device. The distal end includes a housing structure and a cavity within the housing structure. The cavity opens exterior the implantable medical device via a distal opening. The monolithic controlled release device is within the cavity and proximal the distal opening. The monolithic controlled release device includes a distal face, a proximal face opposite the distal face, an outer circumferential surface extending between the distal face and the proximal face, and a spline-shaped inner lumen extending between the distal face and the proximal face and radially inward from the outer circumferential surface. The monolithic controlled release device further includes an active pharmaceutical ingredient.

In one embodiment, the implantable medical device includes a passive fixation cardiac lead, an active fixation cardiac lead, or a leadless pacemaker.

In one embodiment, the implantable medical device includes a passive fixation cardiac lead including a tip electrode. The distal opening is a through-hole extending through the tip electrode.

In one embodiment, the implantable medical device includes an active fixation cardiac lead including a helical active fixation anchor distally extending from the cavity. The monolithic controlled release device is located within at least one helical coil of the helical active fixation anchor.

In one embodiment, the implantable medical device includes a leadless pacemaker including a tip electrode. The distal opening is a through-hole extending through the tip electrode.

In one embodiment, the spline-shaped inner lumen includes ridges extending longitudinally along an inner surface of the spline-shaped inner lumen. The spline-shaped inner lumen also includes grooves extending longitudinally along the inner surface of the spline-shaped inner lumen. The ridges and grooves may be circumferentially dispersed along an inner circumference of the spline-shaped inner lumen in an alternating arrangement.

The ridges project radially inward towards a longitudinal center line of the spline-shaped inner lumen. The ridges may be radiused and have the appearance of half-cylinders extending along the spline-shaped inner lumen. Each radiused ridge may have a curvature radius of 0.005 inch, plus or minus about 0.001 inch.

The grooves extend radially outward from the longitudinal center line of the spline-shaped inner lumen and into a wall structure of the monolithic controlled release device to terminate at bottoms, which may be planar. In one embodiment, the grooves extend into the wall structure of the monolithic controlled release device to terminate at planar bottoms having the appearance of a rectangle extending along the spline-shaped inner lumen. Each planar-bottom may have a width of 0.034 inch, plus or minus 0.002 inch.

In one embodiment, the distal face and proximal face are planar, and the outer circumferential surface is cylindrical and smooth. In other embodiments, at least one of the distal face, proximal face, or outer circumferential surface is ridged and grooved as opposed to planar.

In one embodiment, the spline-shaped inner lumen includes eight ridges and eight grooves arranged in equal alternating fashion about the inner circumference of the spline-shaped inner lumen. The eight ridges are circumferentially spaced apart from each other by an angle of 45 degrees.

In one embodiment, the spline-shaped inner lumen has an opposing ridge crest-to-crest diameter of 0.026 inch, plus or minus about 0.002 inch.

In one embodiment, the monolithic controlled release device is an injection molded mixture of active pharmaceutical ingredient and a mixture containing at least liquid silicone rubber. The active pharmaceutical ingredient may include at least one of Dexamethasone Sodium Phosphate or Dexamethasone Acetate.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

The following discussion is directed to implantable cardiac rhythm management devices (ICRMD) employing monolithic controlled release devices (MCRD) carrying an active pharmaceutical ingredient (API). The ICRMD may be in the form of an implantable cardiac lead for pacing and/or defibrillation. Such leads may be configured for passive or active fixation. The ICRMD may alternatively be in the form of a leadless pacemaker.

As discussed in detail below, the MCRD is configured to provide improved eluent access through a MCRD inner lumen with a spline-shaped transverse cross-sectional profile. This spline-shaped profile increases the available eluent contact surface area as compared to a typical cylindrical inner lumen with a circular transverse cross-sectional profile. Further, the spline-shaped profile channels the contact surfaces deeper into the walls of the MCRD. All of this combines to provide improved drug release consistency and greater ease of release of the overall percentage of API. Improved consistency and greater drug release improves MCRD yield, reduces product scrap, and provides more consistent anti-inflammatory treatment by the API at the implant site.

a) Splined Monolithic Controlled Release Device (MCRD)

Figure 1:
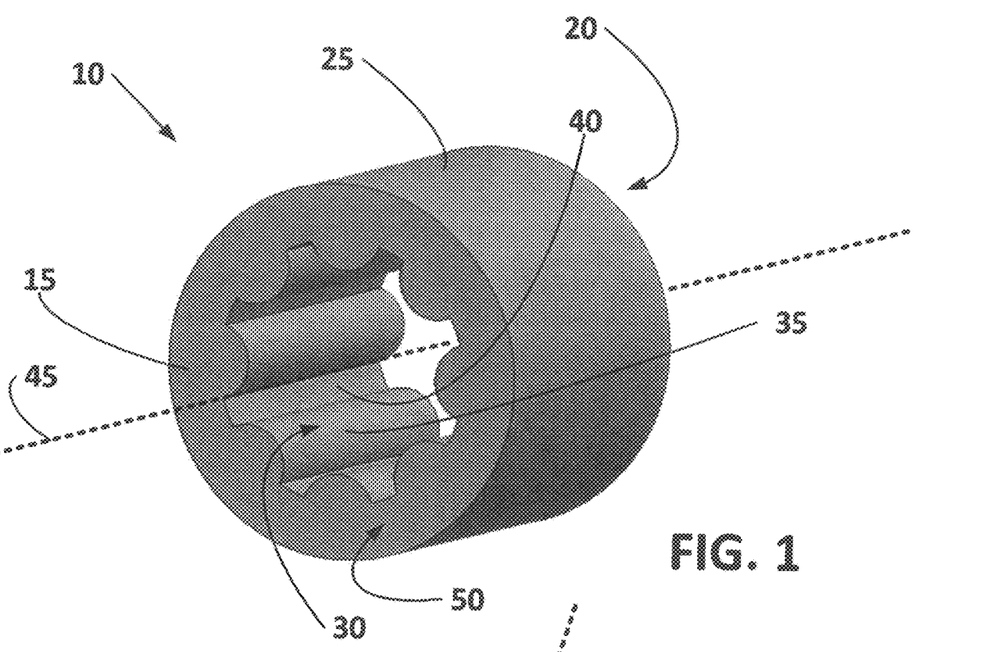
FIG. 1 is a perspective view of an example monolithic controlled release device (MCRD) having an inner lumen with a spline-shaped transverse cross-sectional profile.
Figure 2:
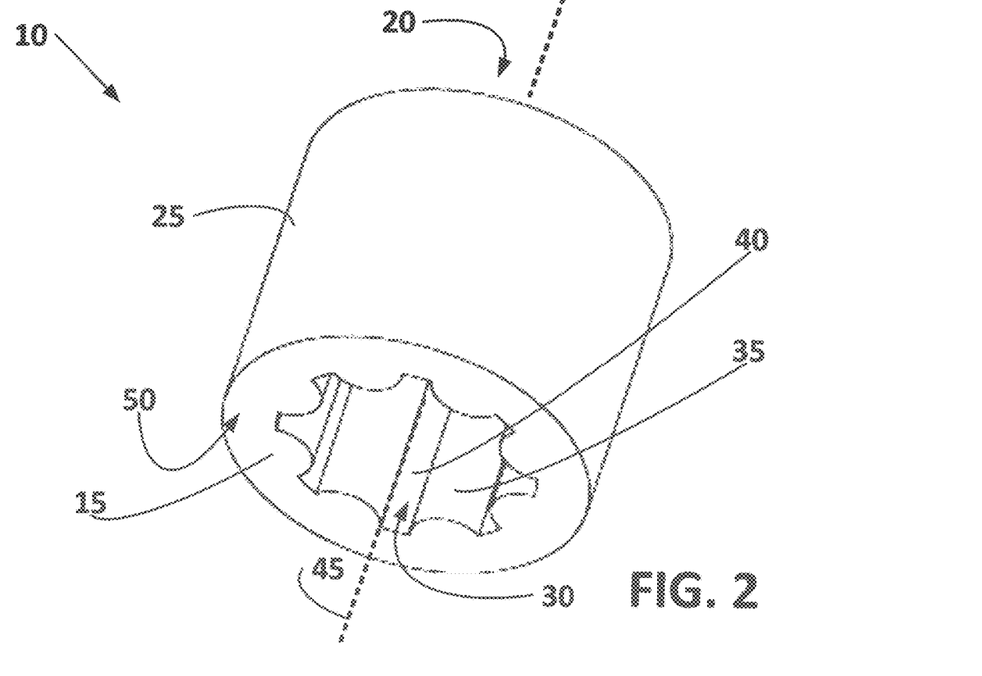
FIG. 2 is another perspective view of the MCRD of FIG. 1.

To begin a detailed discussion of an example splined MCRD 10, reference is made to FIGS. 1 and 2, which are different perspective views of the MCRD 10. As can be understood from FIGS. 1 and 2, in one embodiment, MCRD 10 includes a distal face 15, a proximal face 20, an outer circumferential surface 25, and a spline-shaped inner lumen 30. The proximal face 20 is opposite the distal face 15. The outer circumferential surface 25 extends between the distal face and the proximal face. The spline-shaped inner lumen 30 extends between the distal face 15 and the proximal face 20 and is radially inward from the outer circumferential surface 25.

The spline-shaped inner lumen 30 includes arcuate or radiused ridges 35 and planar-bottomed grooves 40, both of which extend longitudinally along the inner surface of the lumen 30. The ridges 35 and grooves 40 are circumferentially dispersed along the inner circumference of the lumen 30 in an alternating arrangement. The ridges 35 project radially inward towards a longitudinal center line 45 of the lumen 30 and have the appearance of half-cylinders extending along the spline-shaped inner lumen. The grooves 40 extend radially outward from the longitudinal center line 45 of the lumen 30 and into the wall structure 50 of the MCRD 10 to terminate at planar bottoms having the appearance of a rectangle extending along the spline-shaped inner lumen.

In one embodiment, the distal face 15 and proximal face 20 are planar, and the outer circumferential surface 25 is cylindrical. Thus, the outer surfaces 15, 20, 25 of the MCRD 10 combine to form an overall cylindrical outer shape. However, in other embodiments, one or more of the outer surfaces 16, 20, 25 may be ridged/grooved similar to the ridged/grooved arrangement of the spline-shaped inner lumen 30 as opposed to the smooth surfaces depicted in FIGS. 1 and 2. Such ridged/grooved outer surfaces 15, 20, 25 may increase the surface area available for interaction between effluent (e.g., patient blood) and the API impregnated MCRD 10.

Figure 3:
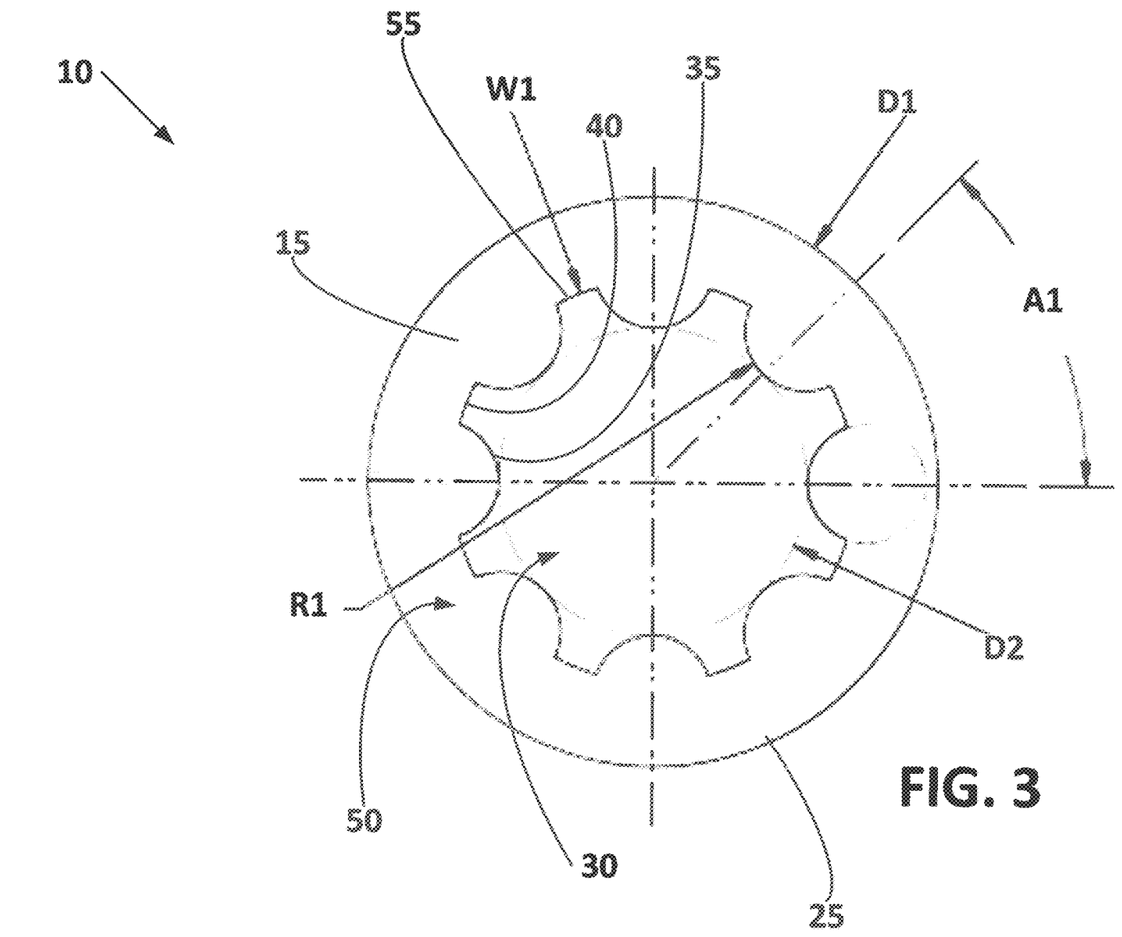
FIG. 3 is an end view of the MCRD of FIGS. 1 and 2.

As shown in FIG. 3, which is an end view of the MCRD 10 of FIGS. 1 and 2, in one embodiment the spline-shaped lumen 30 includes eight radiused ridges 35 and eight planar-bottomed grooves 40 arranged in equal alternating fashion about the inner circumference of the lumen 30. In other embodiments, there may be more or less ridges 35 and grooves 40, although they will still be arranged in equal alternating fashion.

In the embodiment depicted in FIG. 3, the eight radiused ridges 35 are circumferentially spaced apart from each other by an angle A1 of 45 degrees. Of course, the eight planar-bottom grooves 40 are circumferentially spaced apart from each other by the same 45 degrees. In other embodiments where there or more or fewer ridges and grooves, the angle A1 will be correspondingly smaller or larger.

Figure 4:
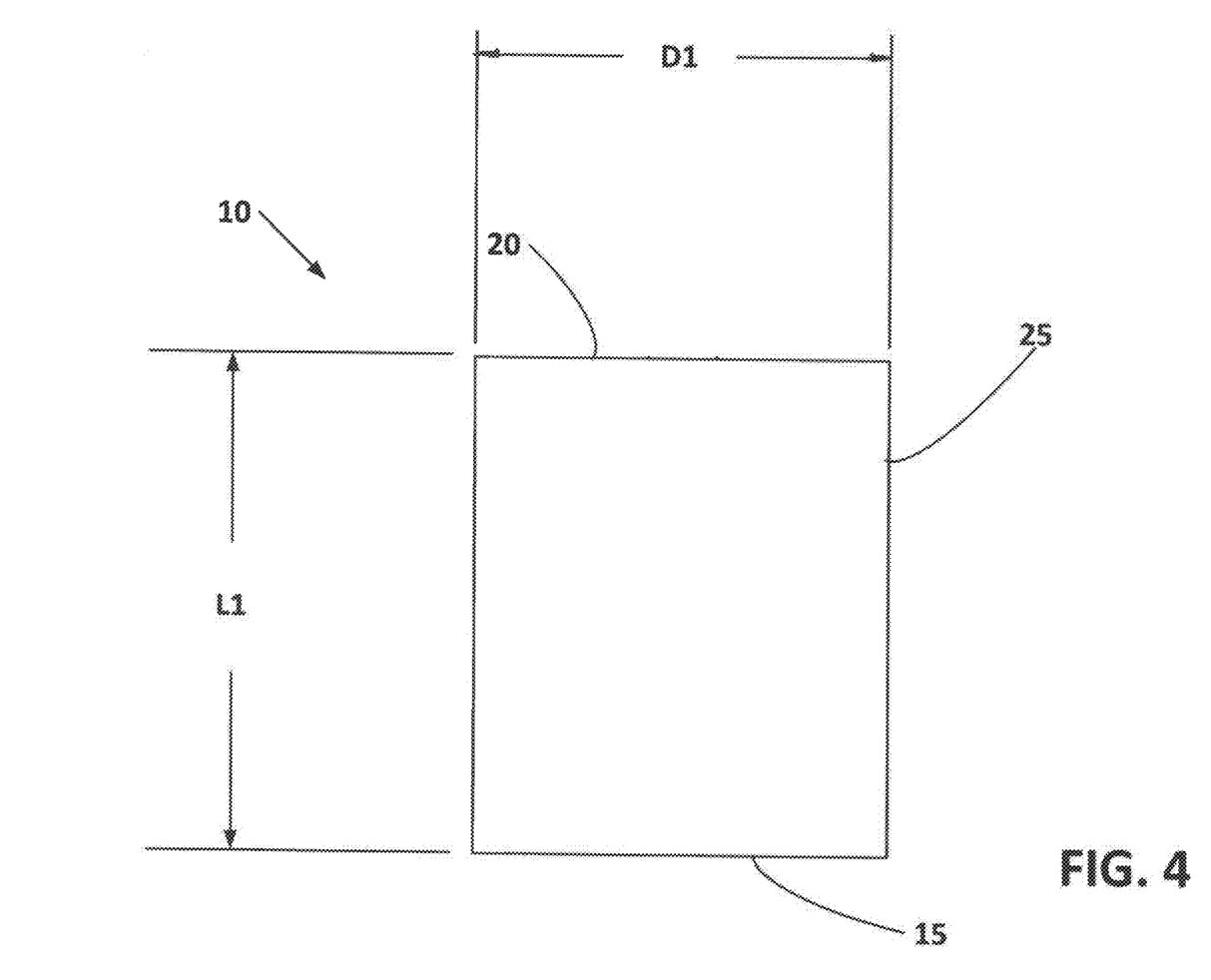
FIG. 4 is a side view of the MCRD of FIGS. 1 and 2.

In one embodiment, as depicted in FIG. 3 and, also FIG. 4, which is a side view of the MCRD 10, the outer circumferential surface 25 of the MCRD 10 has a diameter D1 of 0.048 inch, plus or minus about 0.002 inch. As indicated in FIG. 4, the MCRD 10 from distal face 15 to proximal face 20 has a length of 0.061 inch, plus or minus 0.003 inch.

As illustrated in FIG. 3, the lumen 30 from the crest of opposing radiused ridges 35 has a diameter D2 of 0.026 inch, plus or minus about 0.002 inch. Each radiused ridge 35 also has a curvature radius R1 of 0.005 inch, plus or minus about 0.001 inch. Each planar-bottom groove 40 has a planar bottom 55 with a width W1 of 0.034 inch, plus or minus 0.002 inch. Of course, in other embodiments where there are a greater or lesser number of ridges and grooves, the dimensions A1, D1, D2, L1, R1 and W1 may vary from those recited herein and still remain with the scope of the inventive aspects provided in this detailed description.

In one embodiment, the splined MCRD 10 is manufactured by injection molding an API/liquid silicone rubber mixture over a spline-shaped core pin. The splined MCRD 10 can be implemented with different API materials (e.g., Dexamethasone Sodium Phosphate, Dexamethasone Acetate, or etc.) and can be assembled into active leads, passive leads or leadless pacemakers, all of which are discussed in greater detail below.

b) Leadless Pacemaker Employing MCRD

Figure 5A:
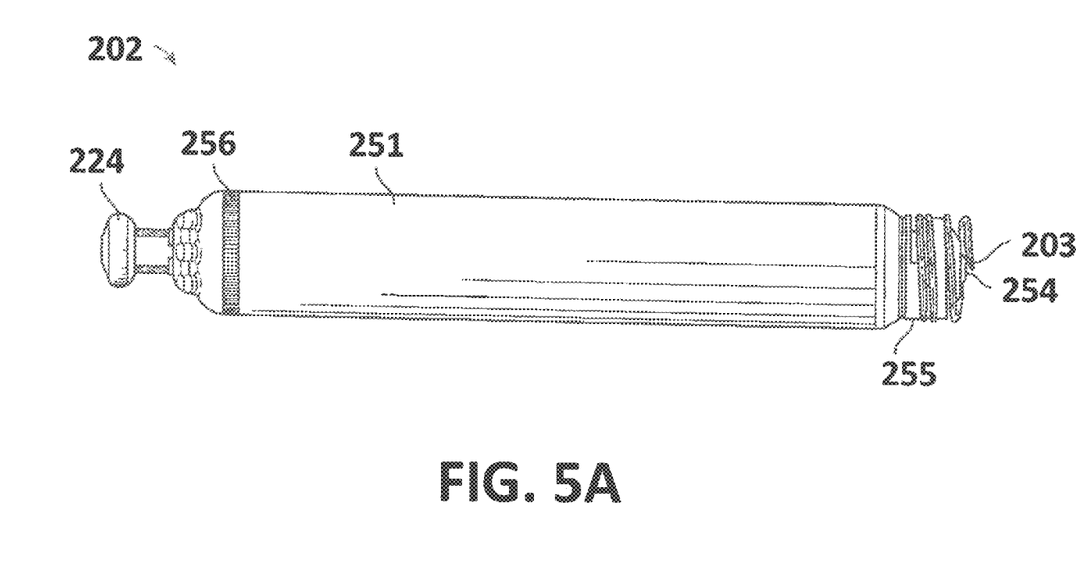
FIGS. 5A and 5B are, respectively, side and end views of an example leadless cardiac pacemaker.
Figure 5B:
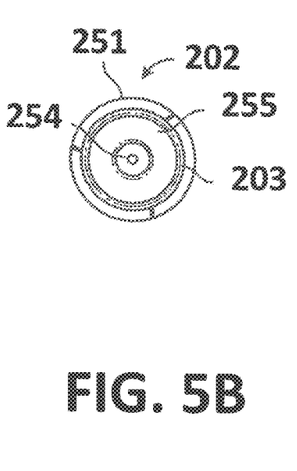

In some embodiments, a splined MCRD 10 may be configured for use with a leadless pacemaker 202 such as that depicted in FIGS. 5A and 5B, which are, respectively side and distal end views of a leadless pacemaker 202. Such leadless pacemakers 202 can communicate by conducted communication, representing a substantial departure from conventional pacing systems. The leadless pacemaker can perform cardiac pacing that has many of the advantages of conventional cardiac pacemakers while extending performance, functionality, and operating characteristics with one or more of several improvements.

As can be understood from FIGS. 5A and 5B, a leadless pacemaker 202 can have two or more electrodes 254, 256 located within, on, or near its hermetic housing 251, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing 251 can optionally contain circuits for sensing cardiac activity from the electrodes 254, 256. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body via a delivery system that may couple with an attachment feature 224 at a proximal end of the housing 251. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Leadless pacemakers or other leadless biostimulators are typically fixed to an intracardial implant site by an actively engaging mechanism or primary fixation mechanism such as a screw or helical member 203 that screws into the myocardium and distally extends from an anchor mount 255 extending from a distal end of the leadless pacemaker. Examples of such leadless biostimulators are described in the following publications, the disclosures of which are incorporated herein in their entireties by reference: (1) U.S. application Ser. No. 11/549,599, filed on Oct. 13, 2006, entitled "Leadless Cardiac Pacemaker System for Usage in Combination with an Implantable Cardioverter-Defibrillator", and published as US2007/0088394A1 on Apr. 19, 2007; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088395A1 on Apr. 19, 2007, (4) U.S. application Ser. No. 11/549,596 filed on Oct. 13, 2006, entitled "Leadless Cardiac Pacemaker Triggered by Conductive Communication" and published as US2007/0088398A1 on Apr. 19, 2007; (5) U.S. application Ser. No. 11/549,603 filed on Oct. 13, 2006 entitled "Rate Responsive Leadless Cardiac Pacemaker" and published as US2007/0088400A1 on Apr. 19, 2007; (6) U.S. application Ser. No. 11/549,605 filed on Oct. 13, 2006, entitled "Programmer for Biostimulator System" and published as US2007/0033405A1 on Apr. 19, 2007; (7) U.S. application Ser. No. 11/549,574, filed on Oct. 13, 2006, entitled "Delivery System for Implantable Biostimulator" and published as US2007/0088418A1 on Apr. 19, 2007; and (8) International Application No. PCT/US2006/040564, filed on Oct. 13, 2006, entitled "Leadless Cardiac Pacemaker and System" and published as WO07047681A2 on Apr. 26, 2007.

Figure 6:
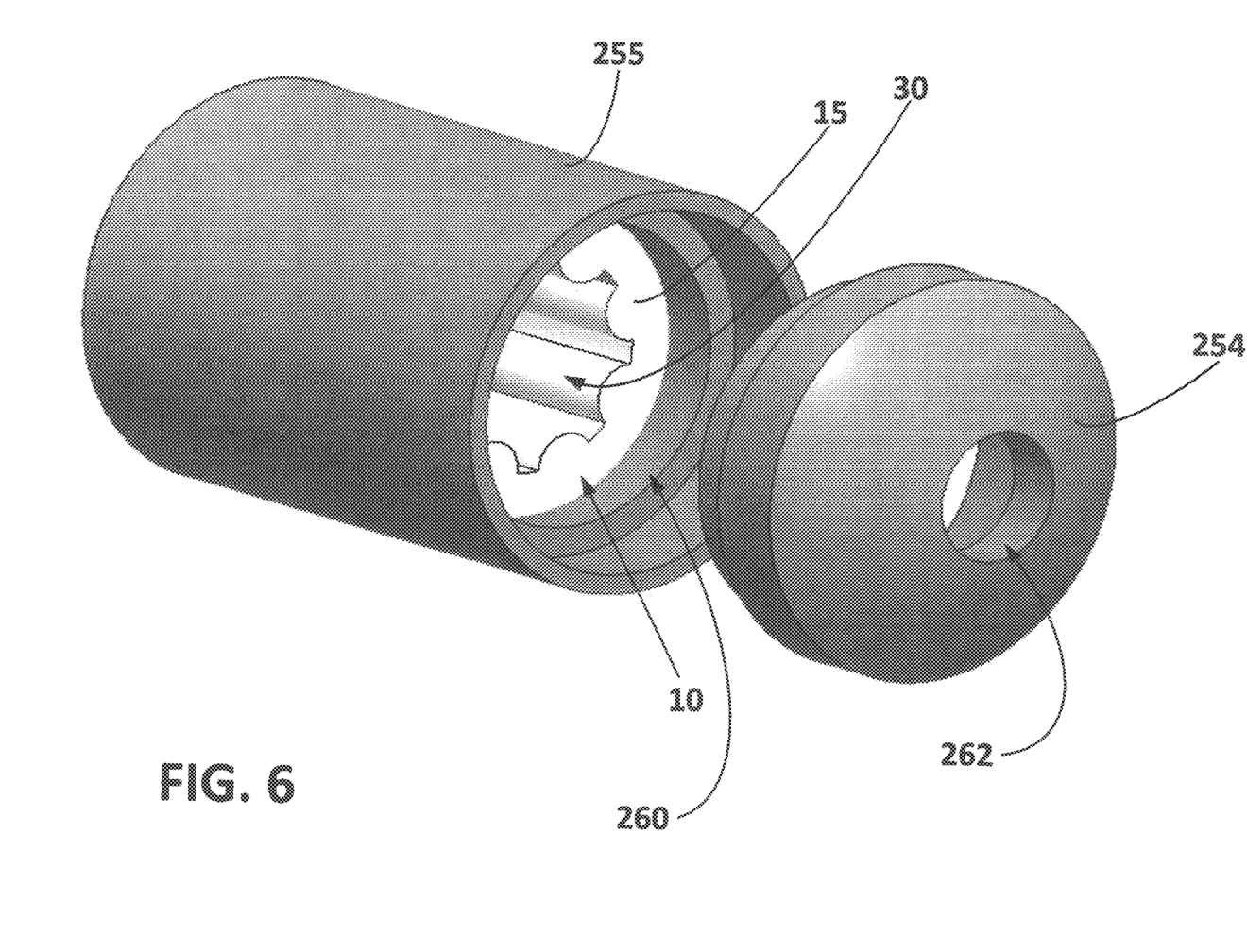
FIG. 6 is a perspective view of the anchor mount and distal tip electrode of the leadless pacemaker of FIGS. 5A and 5B, the electrode being spaced apart from the anchor mount to reveal a cavity behind the tip electrode, the cavity being occupied by the MCRD of FIGS. 1 and 2.

FIG. 6 is a perspective view of the anchor mount 255 and distal tip electrode 254 of the leadless pacemaker of FIGS. 5A and 5B, the electrode 254 being spaced apart from the anchor mount 255 to reveal a cavity 260 behind the tip electrode 254. As shown in FIG. 6, the MCRD 10 can occupy the cavity 260 behind the tip electrode 254. A through-hole 262 extends through the tip electrode 254 to place the cavity 260 in fluid communication with the environment surrounding the exterior of the tip electrode. Thus, the positioning of the MCRD 10 behind the tip electrode 254 allows eluent (e.g., blood) to contact via the through-hole 262 the splined lumen 30 and distal face 15 of the MCRD 10 for release of API.

c) Active and Passive Fixation Implantable Cardiac Leads Employing MCRD

Figure 7:
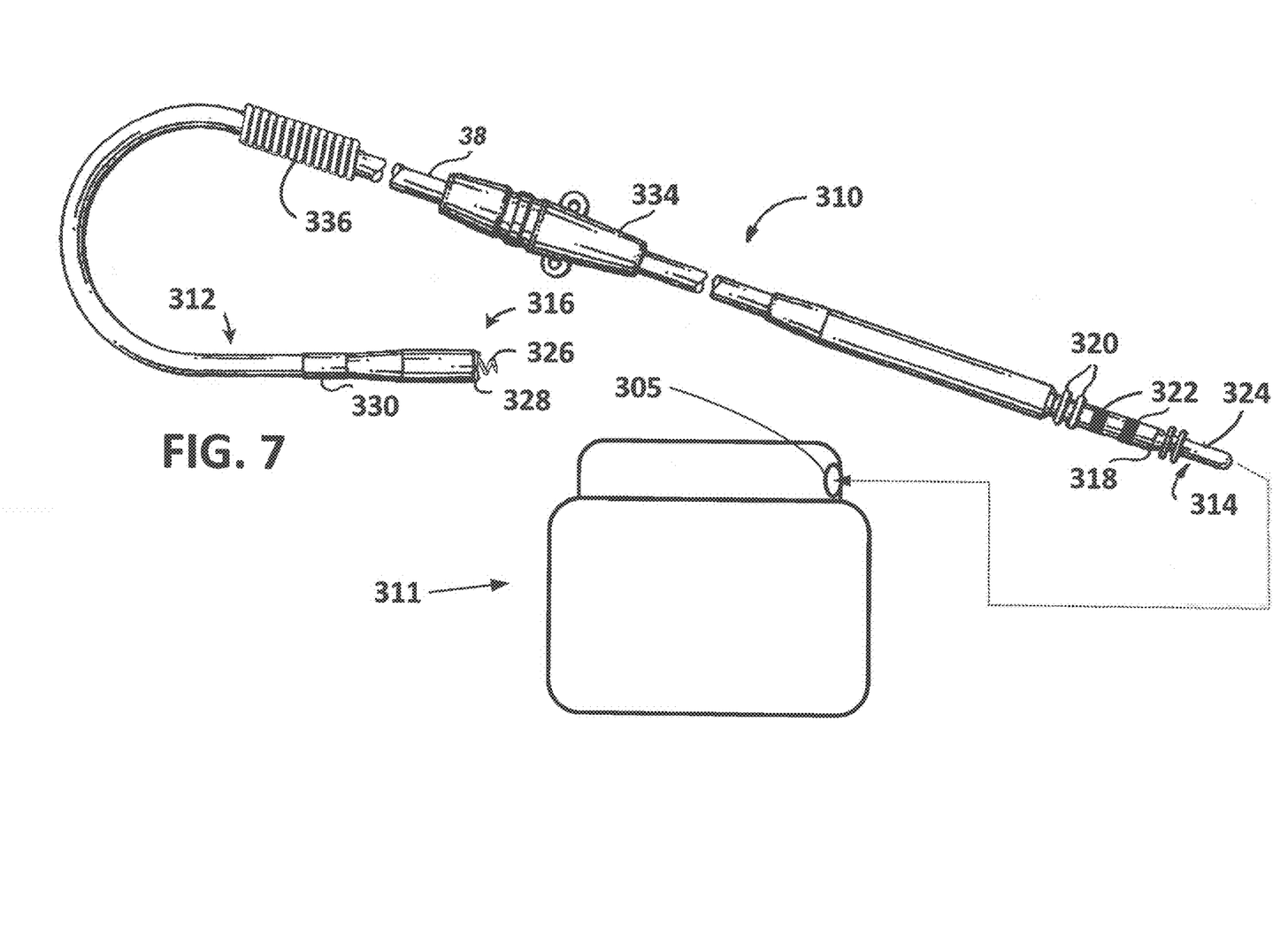
FIG. 7 is a plan view of an embodiment of a lead that is connectable with a pulse generator, wherein an active fixation anchor of the lead is shown in an extended or deployed state.

In some embodiments, a splined MCRD 10 may be configured for use with an implantable cardiac lead 310 such as that depicted in FIG. 7, which is a plan view of an embodiment of a lead 310 that is connectable with a pulse generator 311. As illustrated in FIG. 7, in one embodiment, the lead 310 has an active fixation anchor 326, which is shown in an extended or deployed state. In other embodiments, and as discussed further below, the lead may have a passive fixation configuration at its distal end.

The lead 310 may designed for intravenous insertion and contact with the endocardium, or the lead may be designed for placement external to the heart, for example, in the pericardial space. As indicated in FIG. 7, the lead 310 is provided with an elongated lead body 312 that extends between a proximal region 314 and distal region 316 of the lead 310.

The proximal region 314 of the lead 310 includes a connector assembly 318, which is provided with sealing rings 320 and carries at least one or more electrical connectors in the form of ring contacts 322 and a pin contact 324. The connector assembly 318 is configured to be plugged into a receptacle 305 of the pulse generator 311, the sealing rings 320 forming a fluid-tight seal to prevent the ingress of fluids into the receptacle 305 of the pulse generator 311. When the connector assembly 318 is plugged into the pulse generator receptacle 305, the contacts 322, 324 electrically connect with the circuitry of the pulse generator such that electrical signals can be administered and sensed by the pulse generator via the electrical pathways of the lead 310.

The connector assembly 318 is constructed using known techniques and is preferably fabricated of silicone rubber, polyurethane, silicone-rubber-polyurethane-copolymer ("SPC"), or other suitable polymer. The electrical contacts 322, 324 are preferably fabricated of stainless steel or other suitable electrically conductive material that is biocompatible.

As can be understood from FIG. 7, in some embodiments, the distal region 316 of the lead 310 includes the helical active fixation anchor 326 distally extending from an extreme distal tip end 328 of the lead 310 when the active fixation anchor 326 is in a deployed state. The anchor 326 may be transitioned to a non-deployed state via retraction of the anchor 326 into the confines of the distal region 316 of the lead 310.

The anchor 326 may also be configured to act as an electrode in addition to providing active fixation to heart tissue. Where the anchor 326 is also configured to act as an electrode, depending on the dictates of the pulse generator 311, the anchor 326 may be employed for sensing electrical energy and/or administration of electrical energy (e.g., pacing). The anchor 326 is electrically coupled to the pin contact 324 of the connector assembly 318 via an electrical conductor extending through the lead body 312 and the connector assembly 318.

The distal region 316 of the lead 310 also includes an annular ring electrode 330 proximally offset from the extreme distal tip end 328 of the lead 310. Depending on the dictates of the pulse generator 311, this ring electrode 330 may be employed for sensing electrical energy and/or administration of electrical energy (e.g., pacing). The ring electrode 330 is electrically coupled to one of the ring contacts 322 of the connector assembly 318 via an electrical conductor extending through the lead body 312 and the connector assembly 318.

As depicted in FIG. 7, the lead 310 may include a fixation sleeve 334 slidably mounted around the lead body 312. The fixation sleeve 334 serves to stabilize the pacing lead 310 at the site of venous insertion.

Where the lead 310 is equipped for defibrillation as shown in FIG. 7, a shock coil 336 will be supported on the lead body 312 proximal the ring electrode 330 and distal the fixation sleeve 334. The shock coil 336 is electrically coupled to one of the ring contacts 322 of the connector assembly 318 via electrical conductors extending through the lead body 312.

Figure 8:
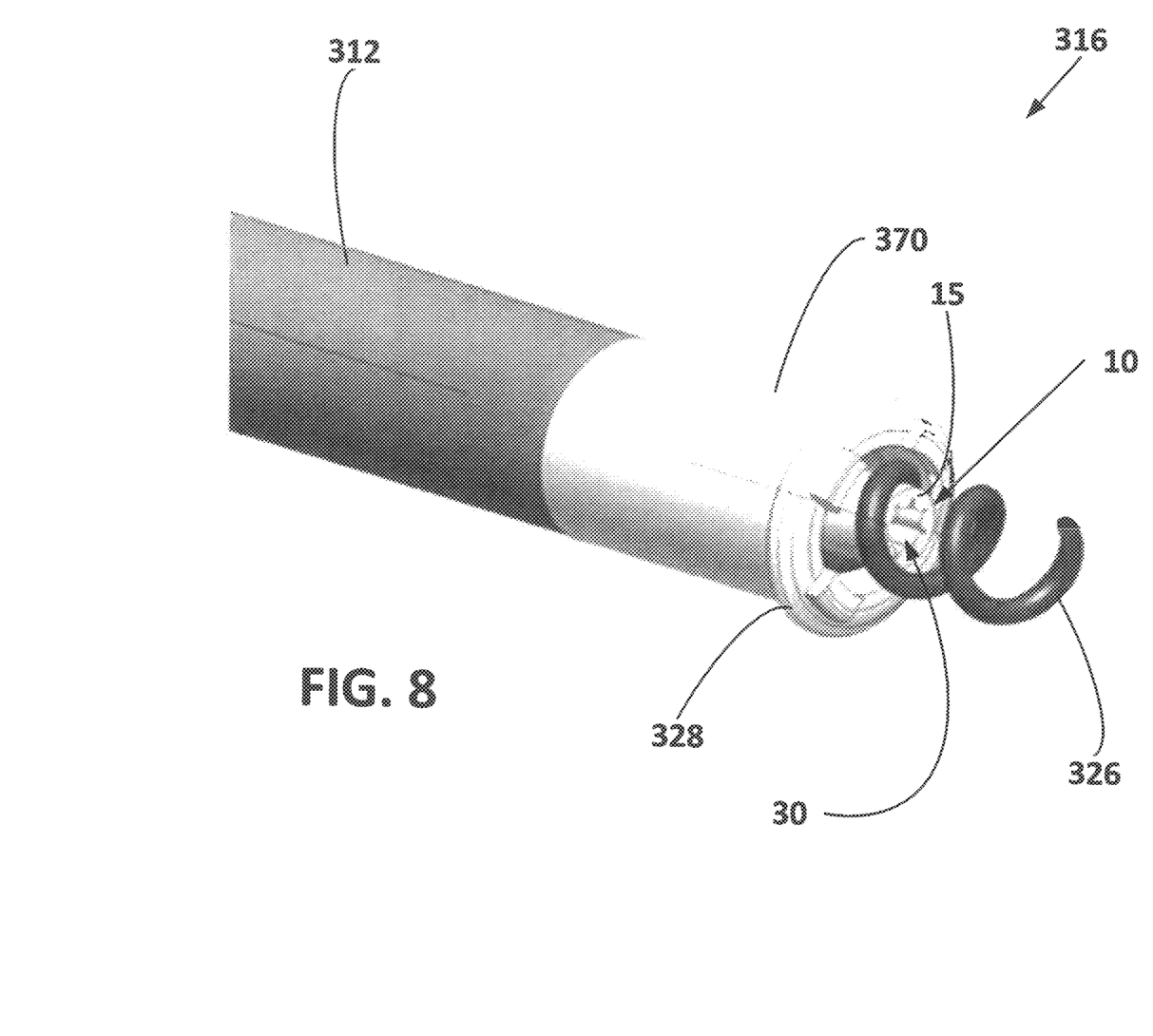
FIG. 8 is an enlarged perspective view of the distal region of the implantable cardiac lead of FIG. 7, the distal region having a helical active fixation anchor with the MCRD of FIGS. 1 and 2 located within the coils of the anchor.

FIG. 8 is an enlarged perspective view of the distal region 316 of the implantable cardiac lead of FIG. 7. As illustrated in FIG. 8, the splined MCRD 10 can be positioned within the helical active fixation anchor 326. The splined MCRD 10 may be fixed with the housing structure 370 of the distal tip 328 of the lead 310 such that the anchor 326 can be extended retracted relative to the distal tip 328 and the splined MCRD 10.

Placement of the splined MCRD 10 within the helical active fixation anchor 326 allows direct contact of the distal face 15 of the spline MCRD 10 with the cardiac wall and brings the splined inner lumen 30 in close proximity to the cardiac wall, thereby facilitating eluent (e.g., blood) to contact the splined lumen 30 and distal face 15 of the MCRD 10 for release of API. The splined inner lumen increases the overall MCRD surface area by approximately 500% as compared to a cylindrical lumen that is not splined.

Figure 9:
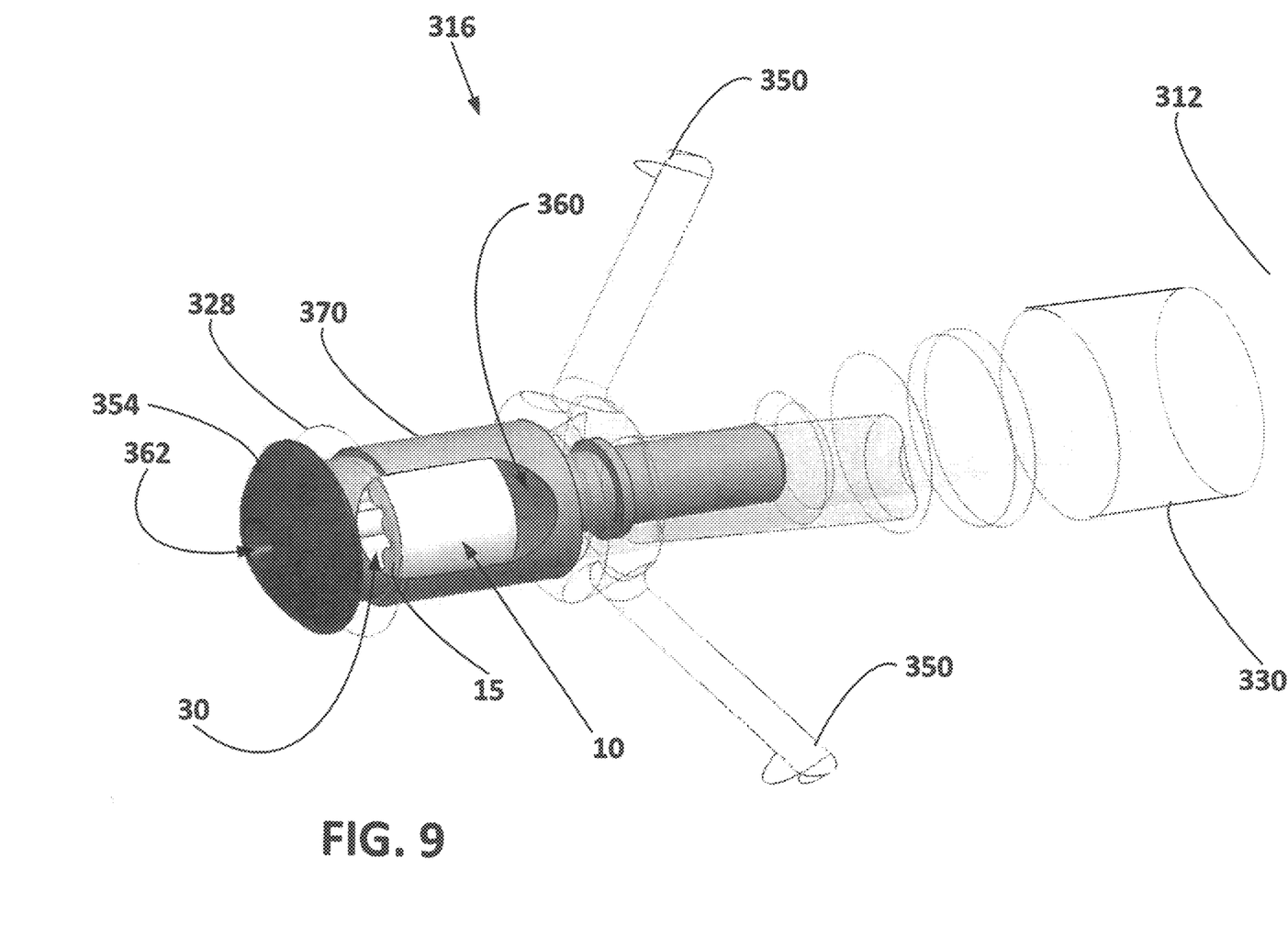
FIG. 9 is a perspective view of the distal region of an implantable cardiac lead similar to that of FIG. 7 except the lead is a passive fixation lead as opposed to an active fixation lead, the by electrode being spaced apart from the distal end of the lead and a portion of the lead being cut away to reveal a cavity behind the by electrode, the cavity being occupied by the MCRD of FIGS. 1 and 2.

FIG. 9 is a perspective view of the distal region 316 of an implantable cardiac lead 310 similar to that of FIG. 7 except the lead 310 is a passive fixation lead as opposed to an active fixation lead, the tip electrode 354 being spaced apart from the distal end 328 of the lead 310 and a portion of the lead being cut away to reveal a cavity 360 behind the tip electrode 354. As shown in FIG. 9, the lead distal region 316 includes passive fixation features 350, which may be in the form of pliable prongs 350 that make atraumatic contact with the cardiac tissue to fix the tip electrode 354 against the cardiac tissue.

As depicted in FIG. 9, the MCRD 10 can occupy the cavity 360 in the housing structure 370 of the distal tip 328, the MCRD 10 being located behind the by electrode 354. A through-hole 362 extends through the tip electrode 354 to place the cavity 360 in fluid communication with the environment surrounding the exterior of the tip electrode. Thus, the positioning of the MCRD 10 behind the tip electrode 354 allows eluent (e.g., blood) to contact via the through-hole 362 the splined lumen 30 and distal face 15 of the MCRD 10 for release of API.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An implantable medical device for implantation against cardiac tissue in the administration of electrotherapy to the cardiac tissue, the device comprising:
   a device body having a distal end including an electrode, the distal end including a housing structure and cavity within the housing structure, the housing structure including a distal opening; and
   a monolithic controlled release device within the cavity and proximal the distal opening, the monolithic controlled release device including:
      a distal face,
      a proximal face opposite the distal face,
      an outer circumferential surface extending between the distal face and the proximal face, and
      a spline-shaped inner lumen extending between the distal face and the proximal face and radially inward from the outer circumferential surface,
   wherein:
      the monolithic controlled release device further includes an active pharmaceutical ingredient, and
      each of the cavity and the spline-shaped inner lumen are open to, and are in fluid communication with as the electrode, an exterior of the device body via the distal opening of the housing structure.

2. The implantable medical device of claim 1, wherein the implantable medical device includes a passive fixation cardiac lead, an active fixation cardiac lead, or a leadless pacemaker.

3. The implantable medical device of claim 1, wherein the spline-shaped inner lumen includes ridges extending longitudinally along an inner surface of the spline-shaped inner lumen.

4. The implantable medical device of claim 3, wherein the spline-shaped inner lumen further includes grooves extending longitudinally along the inner surface of the spline-shaped inner lumen.

5. The implantable medical device of claim 4, wherein the ridges and grooves are circumferentially dispersed along an inner circumference of the spline-shaped inner lumen in an alternating arrangement.

6. The implantable medical device of claim 4, wherein the ridges project radially inward towards a longitudinal center line of the spline-shaped inner lumen.

7. The implantable medical device of claim 6, wherein the ridges are radiused and have the appearance of half-cylinders extending along the spline-shaped inner lumen.

8. The implantable medical device of claim 7, wherein each radiused ridge has a curvature radius of 0.005 inch, plus or minus about 0.001 inch.

9. The implantable medical device of claim 6, wherein the grooves extend radially outward from the longitudinal center line of the spline-shaped inner lumen and into a wall structure of the monolithic controlled release device to terminate at planar bottoms.

10. The implantable medical device of claim 9, wherein the grooves extend into the wall structure of the monolithic controlled release device to terminate at planar bottoms having the appearance of a rectangle extending along the spline-shaped inner lumen.

11. The implantable medical device of claim 10, wherein each planar-bottom has a width of 0.034 inch, plus or minus 0.002 inch.

12. The implantable medical device of claim 1, wherein the distal face and proximal face are planar, and the outer circumferential surface is cylindrical and smooth.

13. The implantable medical device of claim 1, wherein at least one of the distal face, proximal face, or outer circumferential surface is ridged and grooved as opposed to planar.

14. The implantable medical device of claim 1, wherein the spline-shaped inner lumen includes eight ridges and eight grooves arranged in equal alternating fashion about the inner circumference of the spline-shaped inner lumen.

15. The implantable medical device of claim 14, wherein the eight ridges are circumferentially spaced apart from each other by an angle of 45 degrees.

16. The implantable medical device of claim 15, wherein the spline-shaped inner lumen has an opposing ridge crest-to-crest diameter of 0.026 inch, plus or minus about 0.002 inch.

17. The implantable medical device of claim 1, wherein the monolithic controlled release device is an injection molded mixture of active pharmaceutical ingredient and a mixture containing at least liquid silicone rubber, and the active pharmaceutical ingredient includes at least one of Dexamethasone Sodium Phosphate or Dexamethasone Acetate.

18. The implantable medical device of claim 1, wherein the implantable medical device includes a passive fixation cardiac lead including a tip electrode as the electrode, the distal opening being a through-hole extending through the tip electrode.

19. The implantable medical device of claim 1, wherein the implantable medical device includes an active fixation cardiac lead including a helical active fixation anchor distally extending from the cavity, the monolithic controlled release device located within at least one helical coil of the helical active fixation anchor.

20. The implantable medical device of claim 1, wherein the implantable medical device includes a leadless pacemaker including a tip electrode as the electrode, the distal opening being a through-hole extending through the tip electrode.

* * * * *

UNITED STATES PATENT AND TRADEMARK OFFICE
CERTIFICATE OF CORRECTION

PATENT NO. : 10,821,282 B2
APPLICATION NO. : 15/984697
DATED : November 3, 2020
INVENTOR(S) : Tyler J. Strang et al.

It is certified that error appears in the above-identified patent and that said Letters Patent is hereby corrected as shown below:

In the Claims

Column 8, Claim 1, Line 49, after the word "with", delete "as the electrode".

Signed and Sealed this
Fourteenth Day of June, 2022

Katherine Kelly Vidal
*Director of the United States Patent and Trademark Office*